United States Patent
Chen et al.

(10) Patent No.: US 10,954,180 B2
(45) Date of Patent: Mar. 23, 2021

(54) PROCESS FOR ACID-CATALYZED DECOMPOSITION OF ARYL α-HYDROPEROXIDE WITH CONTINUOUS FLOW TUBULAR REACTOR

(71) Applicant: Changzhou University, Changzhou (CN)

(72) Inventors: Qun Chen, Changzhou (CN); Xuan Dai, Changzhou (CN); Mingyang He, Changzhou (CN); Weiyou Zhou, Changzhou (CN); Fu'an Sun, Changzhou (CN); Zhonghua Sun, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 16/561,774

(22) Filed: Sep. 5, 2019

(65) Prior Publication Data
US 2020/0079714 A1    Mar. 12, 2020

(30) Foreign Application Priority Data

Sep. 6, 2018  (CN) .......................... 201811035968.2

(51) Int. Cl.
*C07C 37/08*   (2006.01)
*C07C 39/04*   (2006.01)
(Continued)

(52) U.S. Cl.
CPC .................. *C07C 37/08* (2013.01); *B01J 8/06* (2013.01); *B01J 14/00* (2013.01); *B01J 19/0013* (2013.01);
(Continued)

(58) Field of Classification Search
CPC ..................................................... C07C 37/08
See application file for complete search history.

(56) References Cited

U.S. PATENT DOCUMENTS 5,463,136 A * 10/1995 Blackbourn .............. C07C 1/20
568/385
2008/0086018 A1   4/2008 Cheng et al.
2019/0062245 A1   2/2019 Chen et al.

FOREIGN PATENT DOCUMENTS

| CN | 101006033 A | 7/2007 |
| CN | 101659598 A | 3/2010 |
| CN | 107501050 A | 12/2017 |

OTHER PUBLICATIONS

Translation of Patent No. CN107501050A, Published Dec. 22, 2017, pp. 1-9 (Year: 2017).*

* cited by examiner

*Primary Examiner* — Medhanit W Bahta
(74) *Attorney, Agent, or Firm* — Volpe Koenig

(57) ABSTRACT

The present disclosure relates to a process for acid-catalyzed decomposition of aryl α-hydroperoxide with a continuous flow tubular reactor. The process is a novel process performed in a tubular reactor, taking the aryl α-hydroperoxide such as cumene hydroperoxide (CHP) as a raw material and taking acids as a catalyst, performing acid-catalyzed decomposition of the aryl α-hydroperoxide solution in a short reaction time ranging from tens of seconds to several minutes, thereby obtaining the phenols; wherein an inert component may be filled in the reactor, so that the effects of heat transmission and mass transfer can be enhanced. The aryl α-hydroperoxide and acid are respectively introduced by a metering pump into a mixing module to be mixed, and then enter the tubular reactor to be reacted so as to produce the products such as phenols.

12 Claims, 1 Drawing Sheet

(51) Int. Cl.
*B01J 14/00* (2006.01)
*B01J 19/00* (2006.01)
*B01J 19/24* (2006.01)
*B01J 19/30* (2006.01)
*B01J 8/06* (2006.01)
*C07C 45/53* (2006.01)

(52) U.S. Cl.
CPC ........... *B01J 19/2415* (2013.01); *B01J 19/30* (2013.01); *C07C 45/53* (2013.01); *B01J 2219/00033* (2013.01); *B01J 2219/00087* (2013.01); *B01J 2219/00164* (2013.01); *B01J 2219/00186* (2013.01); *B01J 2219/30215* (2013.01)

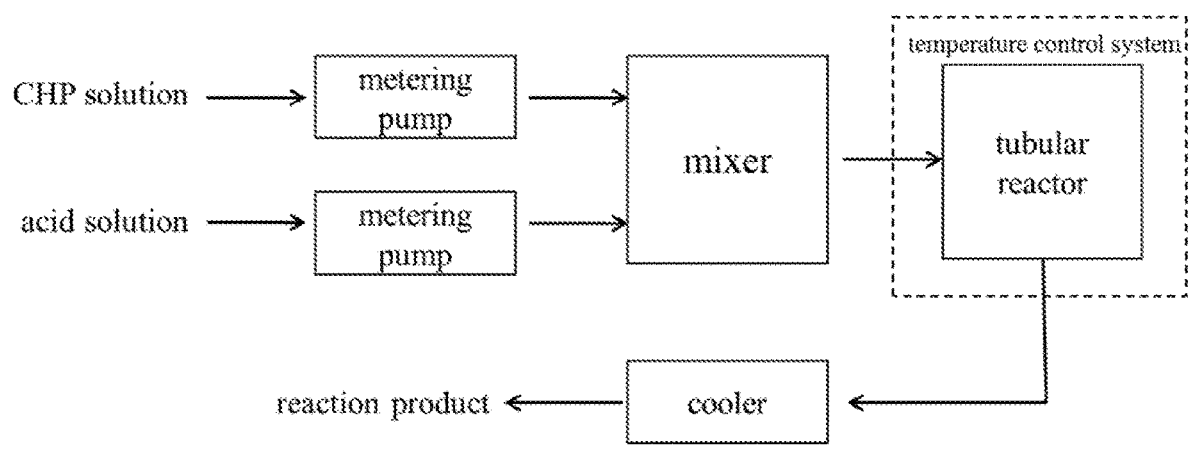

PROCESS FOR ACID-CATALYZED DECOMPOSITION OF ARYL α-HYDROPEROXIDE WITH CONTINUOUS FLOW TUBULAR REACTOR

CROSS REFERENCE

The application claims priority to Chinese Application No. 201811035968.2, filed on Sep. 6, 2018, entitled "Method for Preparing Phenol by Decomposing Cumene Hydroperoxide in Continuous Flow Tubular Reactor", which is herein specifically and entirely incorporated by reference.

TECHNICAL FIELD

The invention belongs to the technical field of peroxide decomposition, and particularly relates to a method of acid-catalyzed decomposition of aryl α-hydroperoxide as a raw material for preparing phenol, polyphenol, aldehydes or ketones, more specifically relates to a process of catalyzing aryl α-hydroperoxide with acid in a continuous flow tubular reactor to produce target product such as phenol or polyphenol.

BACKGROUND

Phenol is a widely used organic chemical raw material, it is mainly used in the production of phenolic resin, caprolactam, bisphenol A, adipic acid, aniline, alkylphenol, salicylic acid and the like; in addition, it can be further used as a solvent and disinfectant such that it is widely used in synthetic fibers, synthetic rubber, plastics, pharmaceuticals, pesticides, perfumes, dyes and coatings. Acetone is also one of the important basic organic raw materials. It is not only a raw material for preparing methyl methacrylate (MMA), methyl isobutyl ketone (MIBK), bisphenol A, isophorone, etc., but also an excellent solvent widely used in medicine, pesticides, coatings and other industries.

Sulfonation method is an early process for preparing phenol, this method is backward and complicated, and causes serious pollution to the environment, thus it has been substantially eliminated. The main disadvantage of toluene-benzoic acid method is low atomic utilization (60.2%) and high cost. Chlorobenzene hydrolysis method is demanding on the operating conditions, as it requires an electrolysis device and the high equipment investment. Along with the continuous advancement of relevant basic research, the production of phenol has gradually evolved from the previous sulfonation method, toluene-benzoic acid method and chlorobenzene hydrolysis method to the cumene process route at present which is more environmentally-friendly with higher production efficiency. Both the sec-butylbenzene method and the process of direct oxidation of benzene are also promising for phenol production at present, but there is still much development space for performing industrial application.

The sec-butylbenzene method uses n-butene as the raw material (CN200580027578.5), n-butene performs alkylation reaction with benzene to generate sec-butylbenzene. The sec-butylbenzene then subjects to oxidation to form hydrogen peroxide sec-butylbenzene, the hydrogen peroxide sec-butylbenzene is further subjected to cleavage to obtain the product, ie, phenol and methyl ethyl ketone (Formula 1).

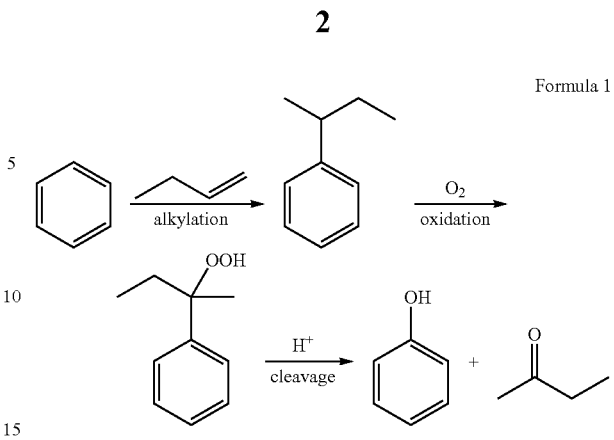

Formula 1

An important value of the sec-butylbenzene method resides in opening up a new approach to utilize n-butene, thereby effectively improving the chemical utilization rate of C4. The sec-butylbenzene method can co-produce methyl ethyl ketone during the process of preparing phenol, which can effectively solve the problem concerning overproduction of acetone and explore a new way in regard to conversion of n-butene. However, the reaction of benzene with n-butene can inevitably produce by-products such as isobutylbenzene, tert-butylbenzene and n-butylbenzene. Given that the by-products have the approximate boiling points, they not only bring difficulties to separation of the products, but also reduce the yield of the target products, and more seriously, these by-products could inhibit the progress of the subsequent oxidation reaction, which is an important reason causing that the sec-butylbenzene method has not been put into large-scale industrialization so far.

The method with one-step oxidation of benzene uses benzene as the raw material, which is subjected to one-step oxidation under the action of a catalyst to prepare phenol (Formula 2) (CN200810119464.9). The process of preparing phenol with one-step oxidation of benzene is characterized by high atomic economy, simple technological process, high yield of product and less environmental pollution, it is an environmentally-friendly organic chemical production process. The process of directly oxidation of benzene is the most simple and convenient way to produce phenol, but the product phenol has a higher electron cloud density than the raw material benzene, and is also prone to perform high-valence oxidation which needs electrons. When molecular oxygen is used as the oxidant and the conversion rate of benzene is about 1%, the selectivity of phenol is within a range of 96%~98%, and the selectivity is decreased when the conversion rate increases. The conversion rate is increased to 13% by using a method of adopting a palladium membrane reactor of alumina MOCVD process, which is equipped with oxygen and benzene at the outside and is provided with hydrogen at the inside, but the selectivity of phenol is decreased. Therefore, there are still many problems towards the industrial application of the process of directly preparing phenol through oxidation of benzene.

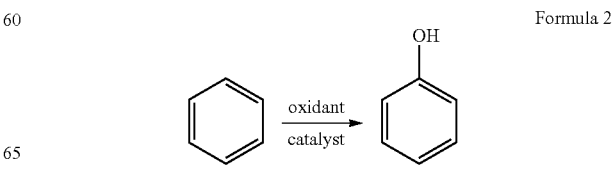

Formula 2

The reaction route of the cumene process is shown in Formula 3: benzene and propylene are initially performed with alkylation reaction to form cumene, the cumene is subject to oxidation in liquid phase to generate CHP, and then the CHP is subject to sulfuric acid-catalyzed decomposition to produce phenol and acetone. Compared with other production methods, the method for producing phenol and acetone with cumene has high quality and low cost, and the equipment corrosion and environmental pollution are very small. By means of this method, these two products phenol and acetone can be simultaneously obtained at a ratio of 1:0.6 in a continuous production process, and a by-product alpha-methyl styrene (AMS) may be continuously produced as a chemical product for sale. At present, the production capacity of phenol by cumene method accounts for more than 95% of the total phenol production capacity in the world.

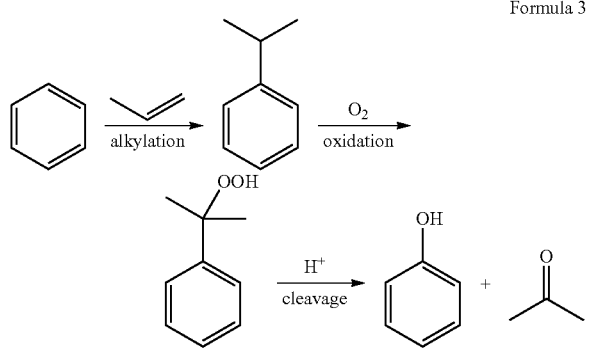

Formula 3

In this process, the step of producing phenol/acetone through the acid-catalyzed decomposition of CHP imposes a significant influence on the product quality and the whole process. Firstly, the reaction is fierce and releases a large amount of heat, it requires a large amount of material circulation to dissipate heat for preventing explosion; secondly, due to the strong acidity, oxidation and dehydration of sulfuric acid, the decomposition has low selectivity, and there are a large amount of by-products such as tar; thirdly, it is necessary to concentrate the CHP raw material to reduce the dosage of sulfuric acid and the degree of corrosion, such a process also increases the operational risk; in the batch reaction process, the by-products increase due to the longer residence time, and the reactor has a huge volume and takes up a large area of the plant.

It is discovered by inventors of the applicant in the previous research that the CHP decomposition reaction by means of micro-channel continuous flow can effectively avoid the above-mentioned problems (CN107501050A). However, the micro-channel reactor has a small pore size and low throughput, which affects the production efficiency in practice, and the equipment is expensive and needs high operational cost. The present disclosure provides a process route for preparing phenol by acid-catalyzed decomposition of CHP in a continuous flow tubular reactor. The tubular reactor used in the invention has a simple structure with cheap equipment and low production cost.

SUMMARY

A purpose of the invention is to provide a process route for acid-catalyzed decomposition of aryl α-hydroperoxide with a continuous flow tubular reactor, wherein one or more components may be filled in the reaction tube to enhance performance of heat transmission and mass transfer. Compared with the traditional tank batch production process, the process of the invention requires simple equipment, the continuous reaction improves the safety and efficiency of production, and the selectivity of the target product such as phenol or polyphenol is greatly improved; as compared with the micro-channel continuous flow process, the continuous flow tubular reactor has an increased throughput and may maintain a high selectivity of the target product.

The invention provides a process for acid-catalyzed decomposition of aryl α-hydroperoxide with a continuous flow tubular reactor, wherein the process comprises the following step (1):

(1) Firstly, the aryl α-hydroperoxide and acid are respectively formed into a homogeneous solution with the solvent; then the aryl α-hydroperoxide solution and the acid solution are synchronously introduced by a metering pump into a mixer for mixing, and the flow rate is controlled to change the molar ratio of aryl α-hydroperoxide to acid to a range of 200:1~1000:1; the mixed solution enters the tubular reactor to carry out reaction, and the temperature is controlled by an external heat exchanger; after the reaction is completed, the obtained product flows out from an outlet of the reactor and is cooled; the residence time is 40 s~240 s, and the reaction temperature is 60° C.~140° C.

In the invention, the aryl α-hydroperoxide is a compound containing one or more substituents expressed by the formula I on a phenyl ring:

Formula I wherein R1 and R2 each independently represent a C1-C5 alkyl group, and optionally, R1 and R2 are bonded to form a ring.

In the invention, the C1-C5 alkyl group includes a C1-C5 linear chain alkyl group and a C3-C5 branched chain alkyl group.

In the invention, the "R1 and R2 are bonded to form a ring" refers to that each of "—CH3" in R1 and R2 removes a hydrogen atom to form a cycloalkyl.

Preferably, R1 and R2 each independently represent a C1-C3 alkyl group, such as methyl, ethyl, n-propyl, isopropyl, or R1 and R2 are bonded to form a cyclohexyl.

The process of the invention preferably further comprises the following step (2):

the concentration of each substance in the reaction products was analyzed by a liquid chromatography external standard method, and the concentration of aryl α-hydroperoxide is titrated by iodometric method.

The conversion of the aryl α-hydroperoxide and the selectivity of the product phenols can be obtained by step (2). Further, when it is necessary to determine the selectivity of the product ketones, this step further comprises analyzing the reaction product by a gas chromatography external standard method.

According to an exemplary embodiment, the invention provides a method for preparing phenol by acid-catalyzed decomposition of CHP in a continuous flow tubular reactor. As shown in the FIGURE, the method is carried out according to the following steps:

(1) Firstly, CHP and acid are each formed into a homogeneous solution with the solvent; then the CHP solution and the acid solution are synchronously introduced by a metering pump into a mixer for mixing, and the flow rate is controlled to change the molar ratio of CHP to acid to a range of 200:1~1000:1; the mixed solution enters the tubular reactor to carry out reaction, and the temperature is controlled by an external heat exchanger; after the reaction is completed, the obtained product is cooled and flows out from the outlet of the reactor; the residence time is 40 s~240 s, and the reaction temperature is 60° C.~140° C.;

(2) the concentration of each substance in the reaction products is analyzed by a liquid chromatography external standard method, and the CHP is titrated by iodometric method. The conversion rate of CHP is 100%, and the yield of phenol is 99% or more.

In step (1), the CHP may be a concentrated cumene oxidizing solution, wherein the solvent is one of acetone, cumene, or a mixture thereof; or the cumene oxidizing solution may be directly used as the source of CHP.

In step (1), the acid may be one or more selected from a group consisting of sulfuric acid, benzenesulfonic acid, methanesulfonic acid and trifluoromethanesulfonic acid.

In step (1), the molar ratio of CHP to acid is preferably 300:1~1000:1, the mass concentration of CHP may be 20%~60%, preferably 20%~40%; and the mass concentration of acid may be 1%~30%, preferably 1%~15%.

In step (1), the reaction residence time in the tubular reactor is preferably 50 s~200 s, and the reaction temperature is preferably within a range of 70° C.~130° C.

In step (1), the mixer may be a micromixer, a static mixer, or other device being capable of performing effective mixing.

In step (1), the tubular reactor has an inner diameter of 0.5 mm~30 mm; the reactor may be filled with one or more components, such as a Raschig ring, a Pall ring, a Nutter ring, a Very Special Packing (VSP) ring, and other inert filler material being capable of enhancing effects of mass transfer and heat transmission.

In addition to CHP, step (1) involving the process route and reaction conditions is also applicable to acid-catalyzed decomposition of other aryl α-hydroperoxide of the invention to form the corresponding phenol, polyphenol, aldehydes or ketones.

Preferably, the process described in step (1) is also used for acid-catalyzed decomposition of sec-butylbenzene hydroperoxide (Formula I-1), cyclohexylbenzene peroxide (Formula I-2), m-diisopropylbenzene hydrogen peroxide (Formula I-3).

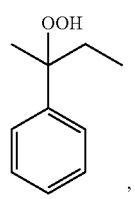

Formula I-1

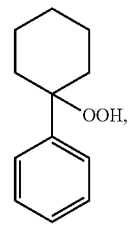

Formula I-2

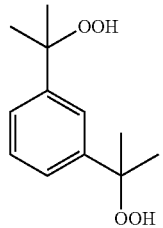

Formula I-1

As compared with the prior art, the invention has the following main features:

1. The invention adopts a continuous flow tubular reactor, the reaction time is shortened from tens of minutes to a range of tens of seconds to several minutes as compared with the traditional tank batch reactor, thereby significantly improving the reaction efficiency; and the selectivity and yield of phenol is kept at a high level; the liquid holdup of the equipment is reduced, the safety factor is increased, and the production cost is lowered.

2. As compared with the micro-channel reaction process, the throughput is increased and the reaction efficiency is improved; the equipment structure is simple and the cost is reduced.

BRIEF DESCRIPTION OF THE DRAWINGS

The FIGURE illustrates a flow chart of the process for preparing phenol by performing acid-catalyzed decomposition of CHP of the invention.

DETAILED DESCRIPTION

In the following Examples 1-13,
selectivity of phenols (phenol, resorcinol)=(molar mass of phenols/molar mass of aryl α-hydroperoxide)×100%;
selectivity of ketones (butanone, cyclohexanone)=(molar mass of ketones/molar mass of aryl alpha-hydroperoxide)×100%.

Examples 1-10 are to illustrate the process for the preparation of phenol by acid-catalyzed decomposition of CHP with a tubular continuous flow reactor. Referring to the technological process of the FIGURE, the following steps are carried out: (1) the CHP solution and the acid solution are respectively introduced by a metering pump into a mixer for mixing, and then introduced into a tubular reactor for reaction, and the system pressure is monitored by a pressure gauge during the whole process; (2) the liquid obtained after the reaction is cooled and collected. The target products and by-products are analyzed by liquid chromatography, and the CHP concentration is titrated by iodometric method.

Examples 11-13 are to illustrate the process for acid-catalyzed decomposition of other aryl α-hydroperoxides with a continuous flow tubular reactor. This process is also carried out with reference to the FIGURE, except that the CHP solution in the FIGURE is replaced by a solution of other aryl α-hydroperoxide. The target products and by-products are analyzed by the liquid chromatography and optionally the gas chromatography, and the aryl α-hydroperoxide concentration is titrated by iodometric method.

Example 1

(1) Apparatus used: a static mixer is used, and the tubular reactor used has an inner diameter of 20 mm.

(2) Acetone is used as a solvent, the mass concentration of the prepared CHP solution is 30%, and the mass concentration of sulfuric acid solution is 2%. The flow rate of the CHP solution is set to 40 mL/min, and the flow rate of the sulfuric acid solution is set to 1 mL/min, both the CHP solution and the sulfuric acid solution are introduced into the mixer to be mixed, and the molar ratio of the CHP to sulfuric acid is 337:1; the mixed raw materials are introduced into the tubular reactor for performing reaction, the reaction temperature is 80° C., and the residence time is 120 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 99.3%, and the total yield of phenol is 99.3%.

Example 2

(1) Apparatus used: a static mixer is used, and the tubular reactor used has an inner diameter of 30 mm and is filled with Pall rings.

(2) Acetone is used as a solvent, the mass concentration of the prepared CHP solution is 29%, and the mass concentration of sulfuric acid solution is 2%. The flow rate of the CHP solution is set to 36 mL/min, and the flow rate of the sulfuric acid solution is set to 0.9 mL/min, both the CHP solution and the sulfuric acid solution are introduced into the mixer to be mixed, the molar ratio of the CHP to sulfuric acid is 337:1; the mixed raw materials are introduced into the tubular reactor for performing reaction, the reaction temperature is 60° C., and the residence time is 120 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 98.9%, and the total yield of phenol is 98.9%.

Example 3

(1) Apparatus used: a static mixer is used, the tubular reactor used has an inner diameter of 0.5 mm.

(2) Acetone is used as a solvent, the mass concentration of the prepared CHP solution is 35%, and the mass concentration of sulfuric acid solution is 2.5%. The flow rate of the CHP solution is set to 36 mL/min, and the flow rate of the sulfuric acid solution is set to 0.9 mL/min, both the CHP solution and the sulfuric acid solution are introduced into the mixer to be mixed, and the molar ratio of the CHP to sulfuric acid is 337:1; the mixed raw materials are introduced into the tubular reactor for performing reaction, the reaction temperature is 140° C., and the residence time is 240 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 97.1%, and the total yield of phenol is 97.1%.

Example 4

(1) Apparatus used: a static mixer is used, and the tubular reactor used has an inner diameter of 8 mm.

(2) Acetone is used as a solvent, the mass concentration of the prepared CHP solution is 30%, and the mass concentration of sulfuric acid solution is 2%. The flow rate of the CHP solution is set to 40 mL/min, and the flow rate of the sulfuric acid solution is set to 0.3 mL/min, both the CHP solution and the sulfuric acid solution are introduced into the mixer to be mixed, and the molar ratio of the CHP to sulfuric acid is 1000:1; the mixed raw materials are introduced into the tubular reactor for performing reaction, the reaction temperature is 110° C., and the residence time is 120 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 96.2%, and the total yield of phenol is 96.2%.

Example 5

(1) Apparatus used: a micromixer is used, and the tubular reactor used has an inner diameter of 4 mm.

(2) Acetone is used as a solvent, the mass concentration of the prepared CHP solution is 36%, and the mass concentration of sulfuric acid solution is 1%. The flow rate of the CHP solution is set to 29.6 mL/min, and the flow rate of the sulfuric acid solution is set to 3.4 mL/min, both the CHP solution and the sulfuric acid solution are introduced into the micromixer to be mixed, the molar ratio of the CHP to sulfuric acid is 200:1; and the mixed raw materials are introduced into the tubular reactor for performing reaction, the reaction temperature is 80° C., and the residence time is 80 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 99.6%, and the total yield of phenol is 99.6%.

Example 6

(1) Apparatus used: a static mixer is used, and the tubular reactor used has an inner diameter of 4 mm.

(2) Cumene is used as a solvent, the mass concentration of the prepared CHP solution is 20%, and the mass concentration of sulfuric acid solution is 2%. The flow rate of the CHP solution is set to 29.6 mL/min, and the flow rate of the sulfuric acid solution is set to 0.7 mL/min, both the CHP solution and the sulfuric acid solution are introduced into the mixer to be mixed, the molar ratio of the CHP to sulfuric acid is 242:1; the mixed raw materials are introduced into the tubular reactor for performing reaction, the reaction temperature is 110° C., and the residence time is 136 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 92.2%, and the total yield of phenol is 92.2%.

Example 7

(1) Apparatus used: a static mixer is used, and the tubular reactor has an inner diameter of 20 mm.

(2) The oxidizing solution of cumene is used as the source of CHP, its mass concentration is 26.4%, and the mass concentration of sulfuric acid is 3% prepared with acetone as a solvent. The flow rate of the CHP solution is set to 40 mL/min, and the flow rate of the sulfuric acid solution is set to 0.7 mL/min, both the CHP solution and the sulfuric acid solution are introduced into to the mixer to be mixed, the molar ratio of the CHP to sulfuric acid is 247:1; the mixed raw materials are introduced into the tubular reactor for performing reaction, the reaction temperature is 80° C., and the residence time is 112 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 97.1%, and the total yield of phenol is 97.1%.

Example 8

(1) Apparatus used: a static mixer is used, the tubular reactor used has an inner diameter of 20 mm and is filled with Pall rings.

(2) Acetone is used as a solvent, the mass concentration of the prepared CHP solution is 36%, and the mass concentration of methanesulfonic acid is 2%. The flow rate of the CHP solution is set to 40 mL/min, and the flow rate of the methanesulfonic acid solution is set to 1 mL/min, both the CHP solution and the methanesulfonic acid are introduced into the mixer to be mixed, the molar ratio of the CHP to methanesulfonic acid is 337:1; the mixed raw materials are introduced into the tubular reactor for performing reaction, the reaction temperature is 90° C., and the residence time is 120 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 96.1%, and the total yield of phenol is 96.1%.

Example 9

(1) Apparatus used: a micromixer is used, the tubular reactor used has an inner diameter of 20 mm and is filled with Pall rings.

(2) Acetone is used as a solvent, the mass concentration of the prepared CHP solution is 60%, and the mass concentration of trifluoromethanesulfonic acid solution is 2.5%. The flow rate of the CHP solution is set to 12 mL/min, and the flow rate of the trifluoromethanesulfonic acid solution is set to 0.5 mL/min, both the CHP solution and the trifluoromethanesulfonic acid solution are introduced into the micromixer to be mixed, the molar ratio of the CHP to trifluoromethanesulfonic acid is 535:1; the mixed raw materials are introduced into the tubular reactor for performing reaction, the reaction temperature is 110° C., and the residence time is 136 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 99.3%, and the total yield of product is 99.3%.

Example 10

(1) Apparatus used: a static mixer is used, the tubular reactor has an inner diameter of 30 mm and is filled with VSP rings.

(2) Acetone is used as a solvent, the mass concentration of the prepared CHP solution is 29%, and the mass concentration of sulfuric acid solution is 30%. The flow rate of the CHP solution is set to 36 mL/min, and the flow rate of the sulfuric acid solution is set to 0.1 mL/min, both the CHP solution and the sulfuric acid solution are introduced into the mixer to be mixed, the molar ratio of the CHP to sulfuric acid is 226:1; the mixed raw materials are introduced into the tubular reactor for performing reaction, the reaction temperature is 60° C., and the residence time is 120 s; after the reaction, the obtained product flows out from an outlet of the reactor in a state of continuous flow and is cooled by passing through a coil water bath.

(3) The product is analyzed by liquid chromatography, and the CHP is titrated by iodometric method. The results show that the conversion rate of CHP is 100%, the selectivity of phenol is 97.9%, and the total yield of phenol is 97.9%.

Example 11

(1) A micro-mixer is used, the tubular reactor has an inner diameter of 30 mm and is filled with Pall rings.

(2) Acetone is used as a solvent, the mass concentration of the prepared sec-butylbenzene hydroperoxide solution is 32%, and the mass concentration of sulfuric acid is 2%. The flow rate of the sec-butylbenzene hydroperoxide solution is set to 32 mL/min, and the flow rate of the sulfuric acid solution is set to 0.8 mL/min, both the sec-butylbenzene hydroperoxide solution and the sulfuric acid solution are introduced into the mixer to be mixed, the molar ratio of the sec-butylbenzene hydroperoxide to sulfuric acid is 337:1; the mixed raw materials are introduced into the tubular reactor for performing reaction, the reaction temperature is 80° C., and the residence time is 135 s; after the reaction, the obtained product flows out from an outlet of the reactor in a state of continuous flow and is cooled by passing through a coil water bath.

(3) The product is analyzed by liquid chromatography and gas chromatography, and the sec-butylbenzene hydroperoxide is titrated by iodometric method. The results show that the conversion rate of sec-butylbenzene hydroperoxide is 100%, the selectivity of phenol is 99.2%, the selectivity of butanone is 99.0%, and the yields of the product phenol and butanone are 99.2% and 99.0%, respectively.

Example 12

(1) A static mixer is used, the tubular reactor has an inner diameter of 20 mm.

(2) Acetone is used as a solvent, the mass concentration of the prepared cyclohyxylbenzene hydroperoxide solution is 40%, and the mass concentration of sulfuric acid solution is 1%. The flow rate of the cyclohyxylbenzene hydroperoxide solution is set to 40 mL/min, and the flow rate of the sulfuric acid solution is set to 0.1 mL/min, both the cyclohyxylbenzene hydroperoxide solution and the sulfuric acid solution are introduced into the mixer to be mixed, the molar ratio of the sec-butylbenzene hydroperoxide to sulfuric acid is 281:1; the mixed raw materials are introduced into the tubular reactor for performing reaction, the reaction temperature is 90° C., and the residence time is 120 s; after the reaction, the obtained product flows out from an outlet of the reactor in a state of continuous flow and is cooled by passing through a coil water bath.

(3) The product is analyzed by liquid chromatography and gas chromatography, and the cyclohyxylbenzene hydroperoxide is titrated by iodometric method. The results show that the conversion rate of cyclohyxylbenzene hydroperoxide is 100%, the selectivity of phenol is 98.8%, the selectivity of cyclohexanone is 99.3%, and the yields of the product phenol and cyclohexanone are 98.8% and 99.3%, respectively.

Example 13

(1) A micro-mixer is used, the tubular reactor has an inner diameter of 20 mm.

(2) Acetone is used as a solvent, the mass concentration of the prepared m-diisopropylbenzene hydroperoxide solution is 11%, and the mass concentration of sulfuric acid solution is 2%. The flow rate of the m-diisopropylbenzene hydroperoxide solution is set to 24 mL/min, and the flow rate of the sulfuric acid solution is set to 0.7 mL/min, both the m-diisopropylbenzene hydroperoxide solution and the sulfuric acid solution are introduced into the mixer to be mixed, the molar ratio of the m-diisopropylbenzene hydroperoxide solution to sulfuric acid solution is 200:1; the mixed raw materials are introduced into the tubular reactor for performing reaction, the reaction temperature is 100° C., and the residence time is 200 s; after the reaction, the obtained product flows out from an outlet of the reactor in a state of continuous flow and is cooled by passing through a coil water bath.

(3) The product is analyzed by liquid chromatography, and the m-diisopropylbenzene hydroperoxide is titrated by iodometric method. The results show that the conversion rate of m-diisopropylbenzene hydroperoxide is 100%, the selectivity of 1,3-dihydroxylbenzene is 95.3%, and the yield of the products is 95.3%.

The invention claimed is:

1. A process for acid-catalyzed decomposition of aryl α-hydroperoxide with a continuous flow tubular reactor, wherein the process comprises:
respectively forming a homogenous solution of the aryl α-hydroperoxide and an acid in a solvent; then synchronously introducing at a flow rate the aryl α-hydroperoxide solution and the acid solution by a metering pump into a mixer for mixing, and controlling the flow rate to change the molar ratio of aryl α-hydroperoxide to acid to a range of 200:1-1000:1; entering the mixed solution into the tubular reactor for a residence time to carry out reaction to obtain product, controlling temperature of the reaction by an external heat exchanger; after the reaction is completed, flowing product out from an outlet of the reactor and cooling the product;
wherein the residence time in the reactor is 40 s-240 s, and the temperature of the reaction is 60° C.-140° C.,
the aryl of the aryl α-hydroperoxide is a phenyl ring, and the aryl α-hydroperoxide is a compound containing one or more substituents expressed by the formula I on the phenyl ring:

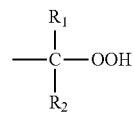

Formula I

R1 and R2 each independently represent a C1-C5 alkyl group, and optionally, R1 and R2 are bonded to form a ring,
the reactor includes one or more component enhancing effects of mass transfer and heat transmission selected from the group consisting of a Raschig ring, a Pall ring, a Nutter ring, and a Very Special Packing (VSP) ring.

2. The process for acid-catalyzed decomposition of aryl α-hydroperoxide with a continuous flow tubular reactor according to claim 1, wherein the aryl α-hydroperoxide is at least one selected from the group consisting of cumyl hydroperoxide (CHP), sec-butylbenzene hydroperoxide expressed by Formula I-1, cyclohexylbenzene peroxide expressed by Formula I-2, and m-diisopropylbenzene hydrogen peroxide expressed by Formula I-3:

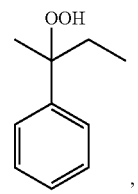

Formula I-1

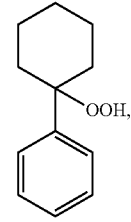

Formula I-2

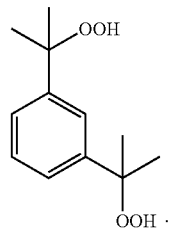

Formula I-3

3. The process for acid-catalyzed decomposition of aryl α-hydroperoxide with a continuous flow tubular reactor according to claim 1, wherein the aryl α-hydroperoxide is cumyl hydroperoxide (CHP).

4. The process for acid-catalyzed decomposition of aryl α-hydroperoxide with a continuous flow tubular reactor according to claim 1, wherein the process further comprises:
analyzing the concentration of each substance in the reaction products by a liquid chromatography external standard method, and the aryl α-hydroperoxide is titrated by an iodometric method.

5. The process for acid-catalyzed decomposition of aryl α-hydroperoxide with a continuous flow tubular reactor according to claim 3, wherein the CHP is a concentrated oxidation liquid of cumene, the solvent is one of acetone and cumene or a mixture thereof; or the oxidation liquid of cumene is used as a source of the CHP.

6. The process for acid-catalyzed decomposition of aryl α-hydroperoxide with a continuous flow tubular reactor according to claim 1, wherein the acid is one or more selected from a group consisting of sulfuric acid, benzenesulfonic acid, methanesulfonic acid and trifluoromethanesulfonic acid.

7. The process for acid-catalyzed decomposition of aryl α-hydroperoxide with a continuous flow tubular reactor according to claim 1, wherein the molar ratio of aryl α-hydroperoxide to acid is 300:1-1000:1, the mass concentration of aryl α-hydroperoxide is 20%-60%, and the mass concentration of acid is 1%-30%.

8. The process for acid-catalyzed decomposition of aryl α-hydroperoxide with a continuous flow tubular reactor according to claim 7, wherein the mass concentration of aryl α-hydroperoxide is 20%-40%.

9. The process for acid-catalyzed decomposition of aryl α-hydroperoxide with a continuous flow tubular reactor according to claim 7, wherein the mass concentration of acid is 1%-15%.

10. The process for acid-catalyzed decomposition of aryl α-hydroperoxide with a continuous flow tubular reactor according to claim 1, wherein the residence time in the tubular reactor is 50 s-200 s, and the temperature of the reaction is within a range of 70° C.-130° C.

11. The process for acid-catalyzed decomposition of aryl α-hydroperoxide with a continuous flow tubular reactor according to claim 1, wherein the mixer is a micromixer or a static mixer.

12. The process for acid-catalyzed decomposition of aryl α-hydroperoxide with a continuous flow tubular reactor according to claim 1, wherein the tubular reactor has an inner diameter of 0.5 mm-30 mm.

* * * * *